US009664597B2

(12) United States Patent
Hofman (10) Patent No.: US 9,664,597 B2
(45) Date of Patent: *May 30, 2017

(54) LIQUID COLLECTION METHODS AND APPARATUSES FOR DETECTING VIRUS DEACTIVATION

(75) Inventor: Jan Hofman, Vlaardingen (NL)

(73) Assignee: ALFA WASSERMANN, INC., West Caldwell, NJ (US)

( * ) Notice: Subject to any disclaimer, the term of this patent is extended or adjusted under 35 U.S.C. 154(b) by 992 days.

This patent is subject to a terminal disclaimer.

(21) Appl. No.: 13/543,951

(22) Filed: Jul. 9, 2012

(65) Prior Publication Data

US 2014/0007711 A1  Jan. 9, 2014

(51) Int. Cl.
  *B01L 3/02* (2006.01)
  *G01N 1/20* (2006.01)
  *G01N 1/18* (2006.01)

(52) U.S. Cl.
  CPC .............. *G01N 1/2035* (2013.01); *G01N 1/18* (2013.01); *G01N 2001/2071* (2013.01)

(58) Field of Classification Search
  CPC .......... G01N 1/10; G01N 1/18; G01N 1/2035; B01F 15/0416; B01F 15/0201
  See application file for complete search history.

(56) References Cited

U.S. PATENT DOCUMENTS

| 3,848,581 A | 11/1974 | Cinqualbre et al. |
| 4,307,620 A | 12/1981 | Jiskoot |
| 4,454,772 A | 6/1984 | Brunner et al. |
| 4,691,850 A | 9/1987 | Kirschmann et al. |
| 5,460,204 A | 10/1995 | Rossi |
| 5,711,916 A | 1/1998 | Riggs et al. |
| 6,032,543 A | 3/2000 | Arthun et al. |

(Continued)

FOREIGN PATENT DOCUMENTS

| CA | 819408 A | 8/1969 |
| CN | 101825559 A | 9/2010 |

(Continued)

OTHER PUBLICATIONS

International Search Report dated Nov. 12, 2013 for PCT application No. PCT/US2013/048221.

(Continued)

*Primary Examiner* — Jill Warden
*Assistant Examiner* — Brittany Fisher
(74) *Attorney, Agent, or Firm* — Ohlandt, Greeley, Ruggiero & Perle, L.L.P.

(57) ABSTRACT

A liquid collection device is provided. The device includes an input conduit, an output conduit, a plurality of product collection containers, and a valve block. The input and output conduits are connectable to a liquid processing line. The valve block has a valve block input in fluid communication with the input conduit, a valve block output in fluid communication with the output conduit, and a plurality of valves. The valves correspond in number to product collection containers and each valve places the input conduit in liquid communication with a different one of the product collection containers. An automated liquid collection workstation for use with the liquid collection device and a method of automatically collecting liquid from a processing line or vessel are also provided.

14 Claims, 8 Drawing Sheets

(56) References Cited

U.S. PATENT DOCUMENTS

| | | |
|---|---|---|
| 6,827,099 B2 | 12/2004 | Tanaka et al. |
| 7,377,686 B2 | 5/2008 | Hubbard |
| 7,381,375 B2 | 6/2008 | Ravkin et al. |
| 7,467,890 B2 | 12/2008 | Patzek, IV |
| 7,560,071 B2 | 7/2009 | Nichols et al. |
| 7,578,205 B2 | 8/2009 | Belongia |
| 7,588,728 B2 | 9/2009 | Clark et al. |
| 7,891,860 B2 | 2/2011 | Hubbard |
| 7,921,740 B2 | 4/2011 | Furey et al. |
| 8,007,743 B2 | 8/2011 | Clark et al. |
| 2001/0010318 A1 | 8/2001 | Saveliev et al. |
| 2001/0048899 A1 | 12/2001 | Marouiss et al. |
| 2002/0037499 A1* | 3/2002 | Quake et al. ............... 435/5 |
| 2003/0116487 A1 | 6/2003 | Petersen |
| 2005/0035138 A1* | 2/2005 | Guerra ................ 221/123 |
| 2007/0023449 A1* | 2/2007 | Belongia et al. ............ 222/64 |
| 2007/0128087 A1 | 6/2007 | Cannizzaro et al. |
| 2008/0130405 A1 | 6/2008 | Hubbard |
| 2010/0154569 A1 | 6/2010 | Guedon |
| 2010/0269918 A1 | 10/2010 | Rudolph |
| 2010/0300563 A1* | 12/2010 | Ramunas et al. ........ 137/565.01 |
| 2011/0024375 A1 | 2/2011 | Reinbigler et al. |
| 2011/0034872 A1* | 2/2011 | Chiravuri et al. ............ 604/132 |
| 2011/0201100 A1 | 8/2011 | Proulx et al. |
| 2012/0000566 A1 | 1/2012 | Morrissey et al. |
| 2012/0061332 A1 | 3/2012 | Kas et al. |
| 2012/0138156 A1* | 6/2012 | Hofman ................ C12M 33/06 137/2 |
| 2012/0223517 A1 | 9/2012 | Morrissey et al. |
| 2012/0315189 A1 | 12/2012 | Scott |

FOREIGN PATENT DOCUMENTS

| | | |
|---|---|---|
| EP | 0086098 | 8/1983 |
| EP | 0637712 | 2/1995 |
| FR | 2358601 | 2/1978 |
| GB | 2445745 | 7/2008 |
| JP | 2003123268 A | 4/2003 |
| JP | 2005170288 A | 6/2005 |
| JP | 2007067968 A | 3/2007 |
| WO | 9009431 | 8/1990 |
| WO | 2007125023 | 11/2007 |
| WO | 2007125023 A1 | 11/2007 |

OTHER PUBLICATIONS

Written Opinion dated Nov. 12, 2013 for PCT application No. PCT/US2013/048221.
Extended European Search Report dated Jul. 12, 2012 for European patent application No. 11009544.5.
Partial Supplementary European Search Report dated May 13, 2016 from corresponding EP Application No. 13816904.0, 7 pages.
Extended European Search Report dated Nov. 8, 2016 from corresponding European Patent Application No. 13816904.0, 14 pages.

* cited by examiner

LIQUID COLLECTION METHODS AND APPARATUSES FOR DETECTING VIRUS DEACTIVATION

CROSS REFERENCE TO RELATED APPLICATIONS

This application is related to U.S. application Ser. No. 12/959,647 filed Dec. 3, 2010 and U.S. application Ser. No. 13/118,891 filed May 31, 2011, the entire contents of both of which are incorporated herein by reference.

BACKGROUND OF THE INVENTION

1. Field of the Invention

The present disclosure relates to automated aseptic liquid collection methods and apparatuses. More particularly, the present disclosure relates to automated aseptic liquid collection methods and apparatuses for detecting virus deactivation.

2. Description of Related Art

The processing of many liquid products must be performed in a sterile environment and/or an aseptic environment to protect the product. Such liquid products can include, but are not limited to, pharmaceutical products (e.g., medicines and vaccines), food products, biological products, biochemical products, chemical products, and any combinations thereof.

The production of some medicines and vaccines requires the use of live viruses or bacteria, which are then subsequently inactivated (i.e., killed or merely weakened) via, for example, the introduction of a chemical or other inactivating mechanism into the production batch. In order to ensure the desired inactivation has been achieved, the batch of liquid is repeatedly tested through a series of samples. The inactivation process can take anywhere from 2 to 24 hours or even longer.

Before inactivation, exposure to the live virus or bacteria can pose a health risk to the personnel in the production area, requiring the use of personal protection devices and systems. Additionally, the production batch must be maintained in a sterile condition before, during, and after inactivation.

Accordingly, it has been determined by the present disclosure that there is a need for workstations that can overcome, alleviate, and/or mitigate one or more of the aforementioned and/or other deleterious effects of the prior art.

BRIEF SUMMARY OF THE INVENTION

A liquid collection device is provided. The device includes an input conduit, an output conduit, a plurality of product collection containers, and a valve block. The input and output conduits are connectable to a liquid processing line. The valve block has a valve block input in fluid communication with the input conduit, a valve block output in fluid communication with the output conduit, and a plurality of valves. The valves correspond in number to product collection containers and each valve places the input conduit in liquid communication with a different one of the product collection containers.

An automated liquid collection workstation is also provided. The workstation includes a processor, a peristaltic pump, a valve actuator, and an algorithm resident on the processor. The valve actuator moves a plurality of valves, when the valves are operatively associated with the valve actuator, between a recirculate position and a collection position. The algorithm is configured to: move all of the plurality of valves to the recirculate position and place the pump in an on state when recirculation is required and move a respective one of the plurality of valves to the collection position for a predetermined collection time period while leaving the pump in the on state when a collection is required.

A method of automatically collecting liquid from a processing line or vessel is provided. The method includes placing an input conduit of a liquid collection device in liquid communication with the processing line or vessel; placing an output conduit of the liquid collection device in liquid communication with the processing line or vessel, the input and output conduits being in fluid communication with a valve block having a plurality of valves; operatively coupling the input conduit to a peristaltic pump; operatively coupling the valve block to a valve actuator so that each of the plurality of valves is movable by a different portion of the valve actuator between a recirculation position and a collection position; controlling the valve actuator to ensure all of the plurality of valves are in the recirculation position and turning on the peristaltic pump so that liquid from the processing line or vessel is pumped through the input conduit, the valve block, and the output conduit back into the processing line; and controlling the valve actuator to move a particular valve of the plurality of valves to the collection position while the peristaltic pump remains on and while at least the valves upstream of the particular valve remain in the recirculate position. The particular valve is associated with a particular collection container so that liquid from the processing line is pumped through the valve block to the particular collection container.

The above-described and other features and advantages of the present disclosure will be appreciated and understood by those skilled in the art from the following detailed description and drawing.

DETAILED DESCRIPTION OF THE INVENTION

Referring to the figures, and in particular to FIGS. 1 through 4, an exemplary embodiment of an automated aseptic liquid collection workstation according to the present disclosure is shown and is generally referred to using reference numeral 10. Workstation 10 is configured to automatically aseptically collect, label, and store, in liquid collection device 12 (shown in FIG. 5), a plurality of liquid collections from a processing line or vessel (A).

Workstation 10 is configured to automatically collect liquids such as, but not limited to, pharmaceutical products (e.g., medicines and vaccines) and any combinations thereof.

Figure 1:
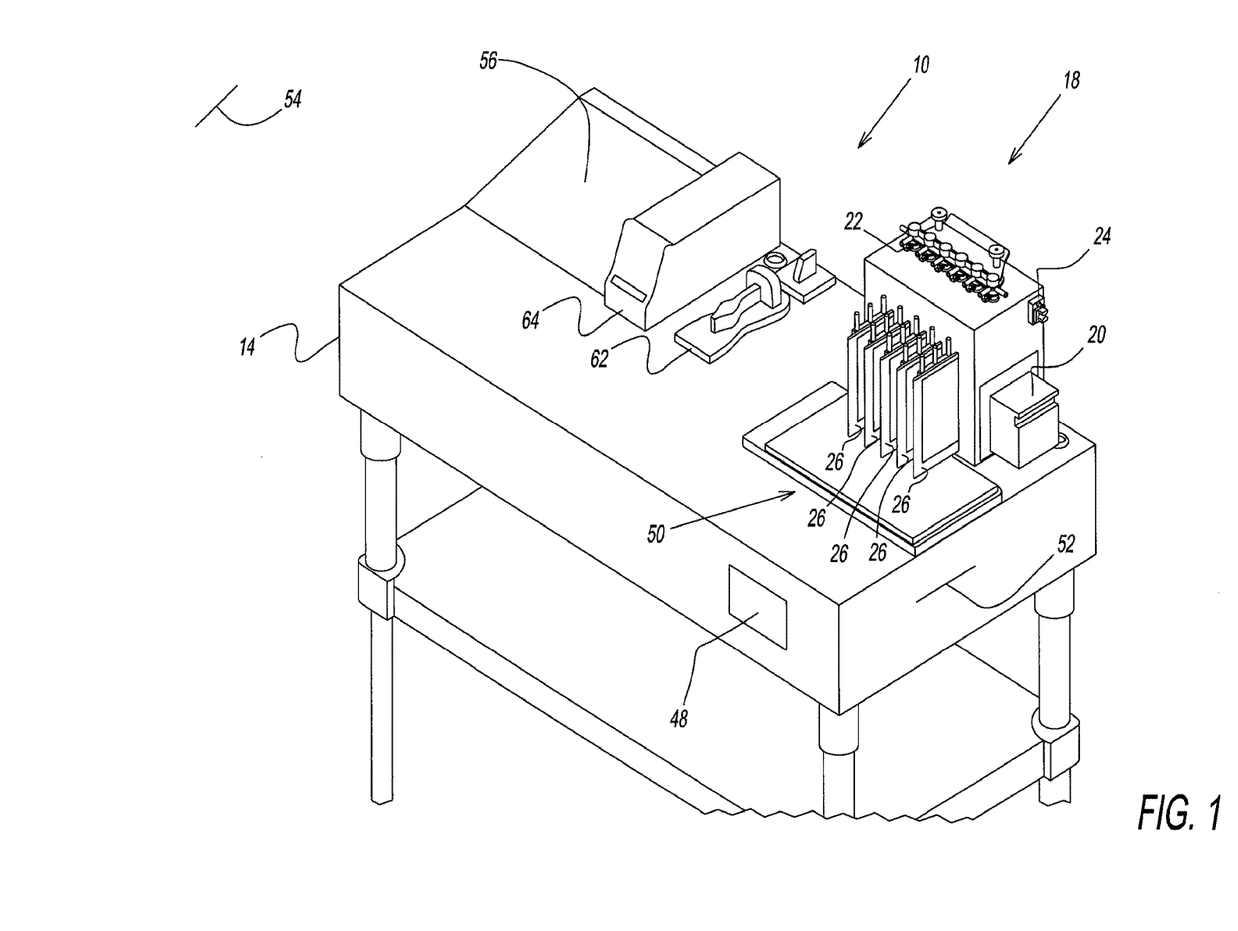
FIG. 1 is a front, top perspective view of an exemplary embodiment of a workstation according to the present disclosure.
Figure 2:
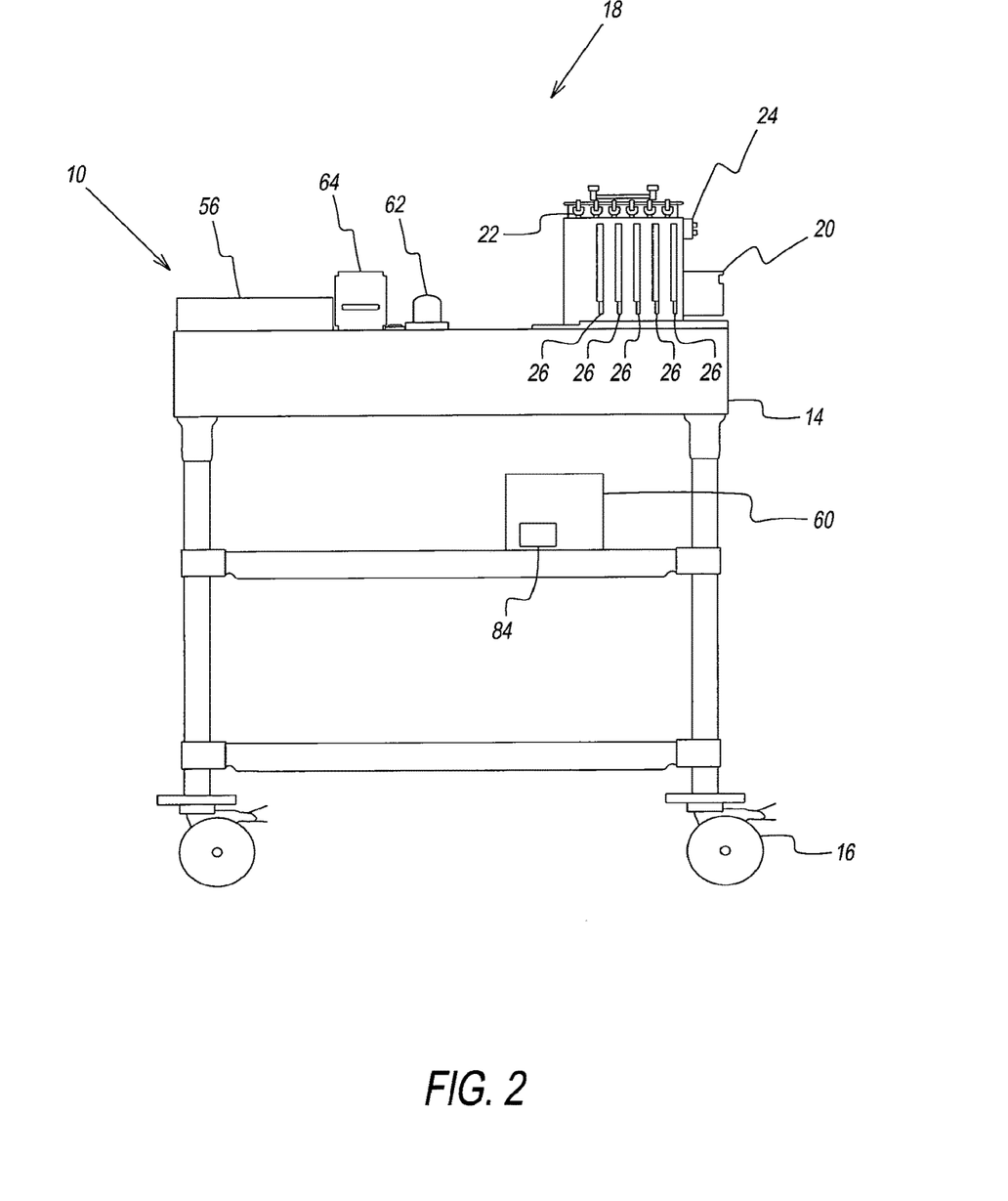
FIG. 2 is a front plan view of the workstation of FIG. 1.
Figure 3:
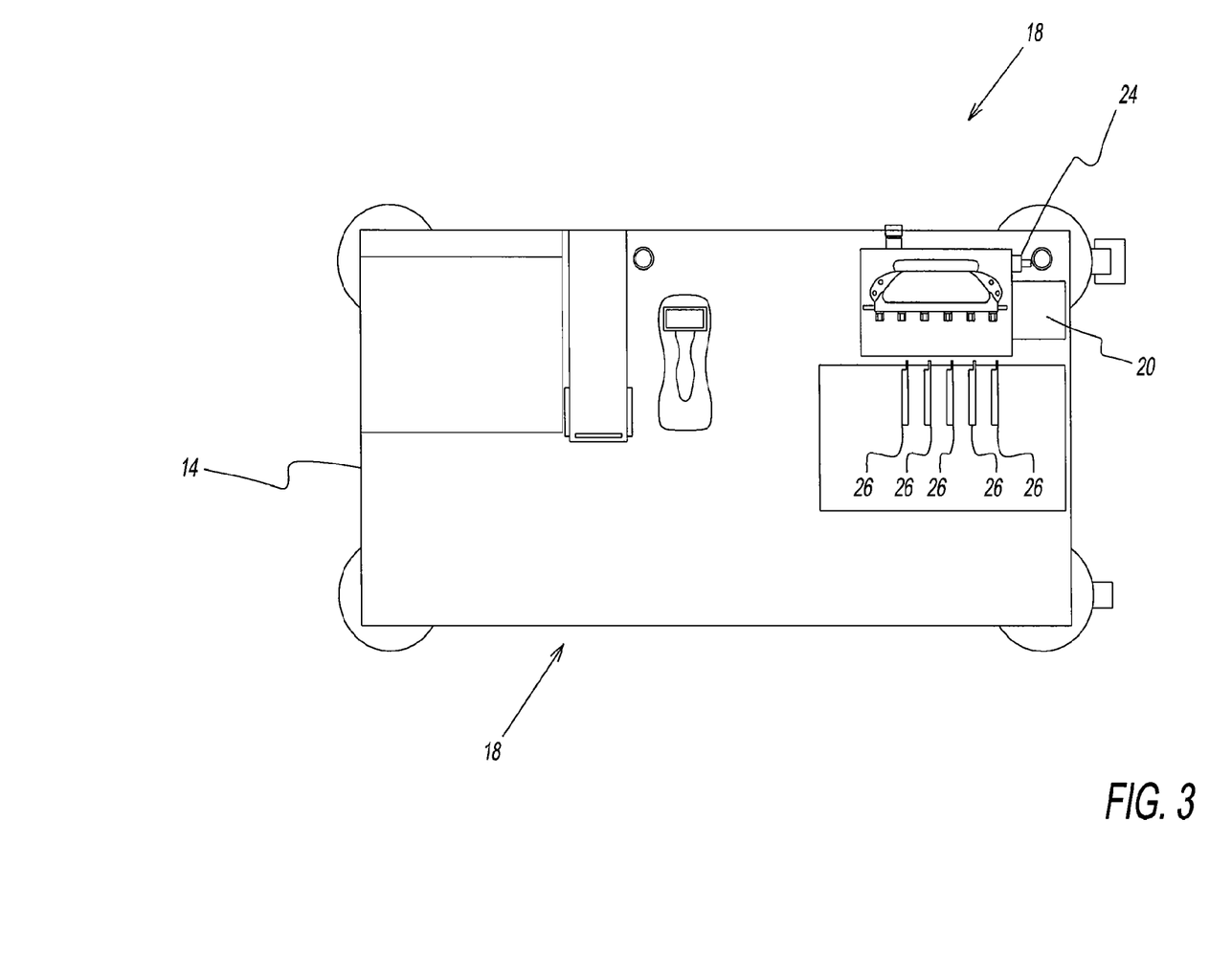
FIG. 3 is a top view of the workstation of FIG. 1.

Workstation 10 includes a base or cabinet 14 supported, in some embodiments, by a plurality of wheels or casters 16 such that the workstation is mobile and can be positioned, as desired, in various locations within a processing facility.

Figure 4:
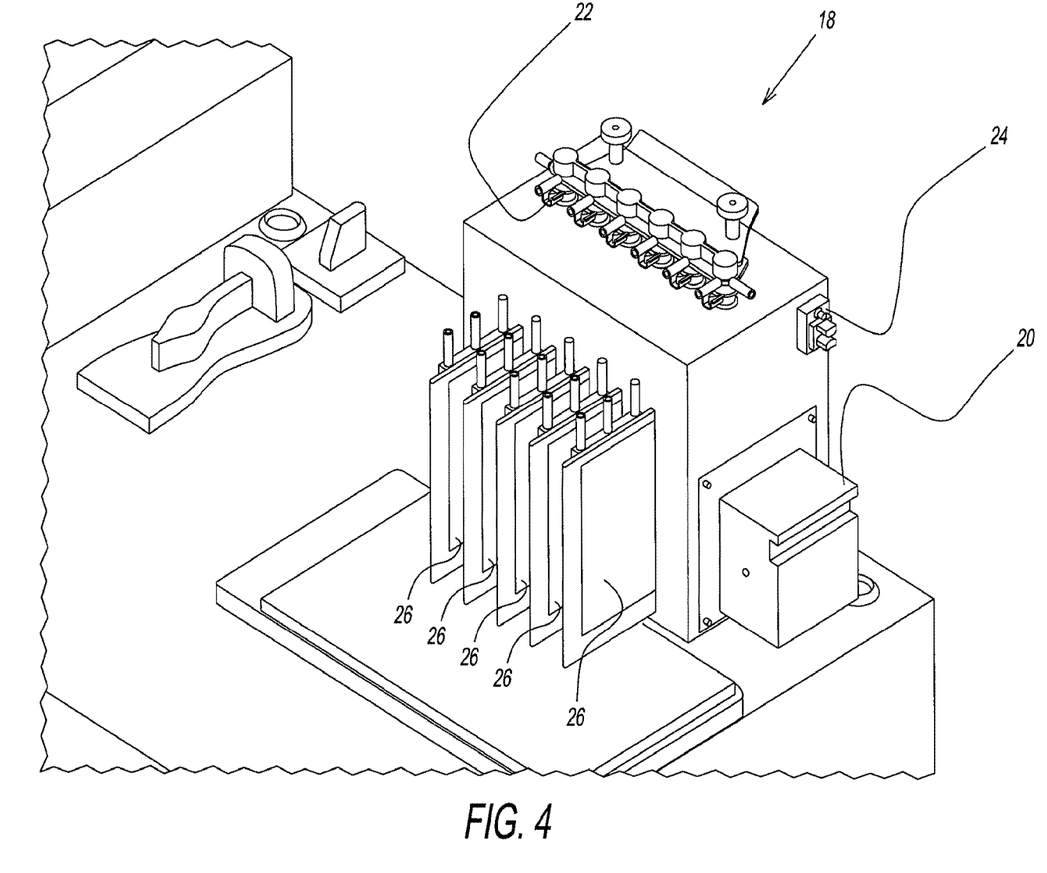
FIG. 4 is a front, top perspective view of an exemplary embodiment of a collection portion of the workstation of FIG. 1.

Workstation 10 is includes collection portion 18 for pumping liquid into collection device 12. Collection portion 18 includes a pump 20, a valve actuator 22, in some embodiments, a liquid edge detector 24, and a plurality of liquid holding areas 26.

Pump 20 can be any desired pumping device but is, preferably, a non-contact pump that selectively draws liquid without directly contacting the liquid itself. In a preferred embodiment, pump 20 is a peristaltic pump.

Figure 5:
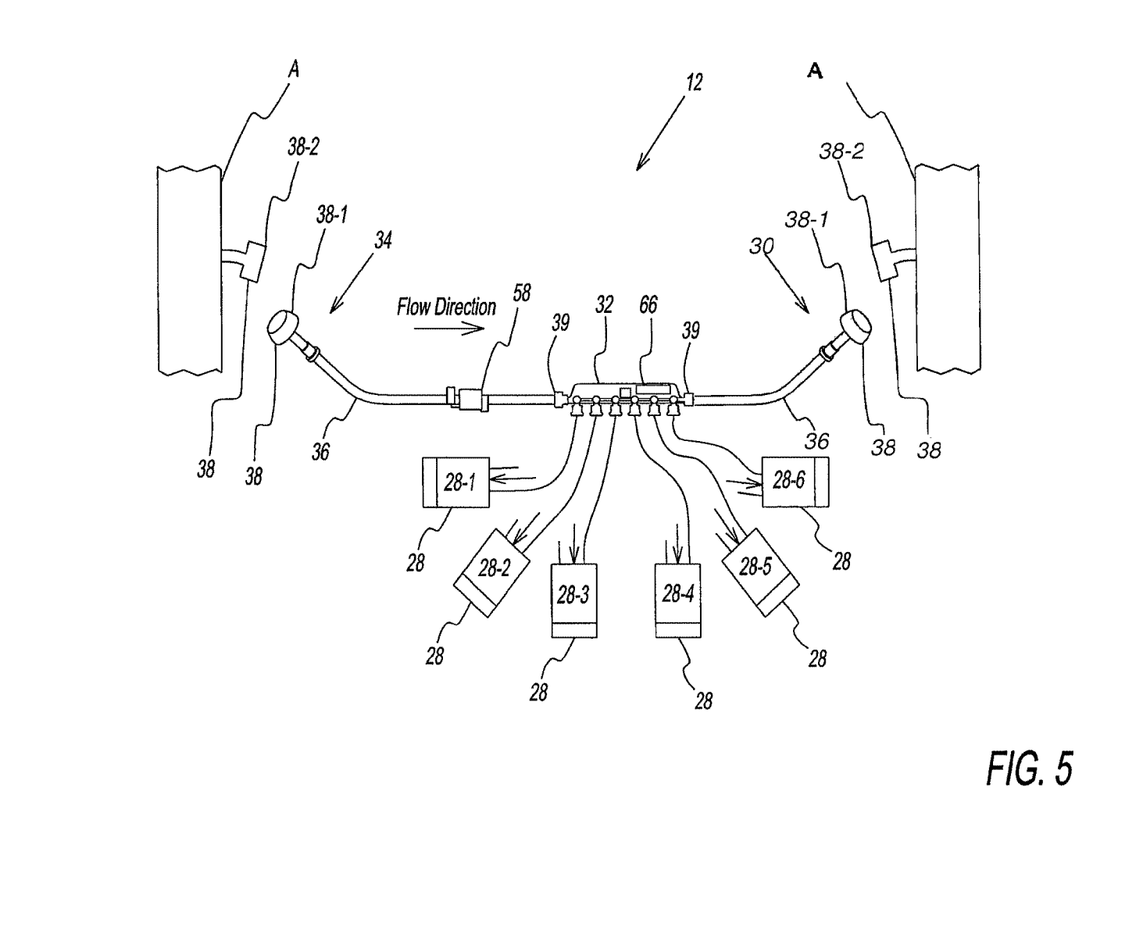
FIG. 5 is a perspective view of an exemplary embodiment of a liquid collection set according to the present disclosure for use with the workstation of FIG. 1.

Liquid edge detector 24 can be any desired detector such as, but not limited to a sonic, a capacitance, or any other non-contacting or contacting sensor for determining the presence and absence of liquid in one or more areas of liquid collection device 12. Detector 24 can be in electrical communication with workstation 10 so that the workstation can detect when liquid is present in a predetermined location in liquid collection device 12.

As seen in FIG. 5, liquid collection device 12 includes a plurality of product collection containers 28 (six shown) and a valve block 32. Product containers 28 can be configured to have any desired volume so that the volumes of the product containers are identical to one another and/or different from one another.

Product collection containers 28 can be any desired collection container such as, but not limited, collection bags as shown in FIG. 5. For example, containers 28 can be collection bags such as the Allegro™ 2D Biocontainer, which is commercially available from Pall Corporation. In this embodiment, each container 28 includes an input line 29 releasably sealed with a clamp 33, an output line 31 releasably sealed with a clamp 33, and a port 35.

Of course, it is contemplated by the present disclosure for containers 28 to be any sterile collection container including, but not limited to, collection bottles, collection boxes, collection syringes, and others.

Device 12 further includes an output conduit 30 and an input conduit 34 configured to place the processing line A in liquid communication with valve block 32.

Input and output conduits 34, 30 each include at least one flexible portion 36, which allow workstation 10 to be easily placed near processing line or vessel (A).

Portion 36 of the input conduit can be configured to operably mate with pump 20 so that the pump can force the liquid into containers 28 of liquid collection device 12. In the example where pump 20 is a peristaltic pump, flexible portion 36 is made of a material having sufficient resiliency (e.g., silicone tubing) to operate in cooperation with the peristaltic pump.

Liquid collection device 12 finds use with two-part, aseptic connectors 38. In the illustrated embodiment, input conduit 34 has only one part 38-1 of a two-part connector 38 connected thereto. Similarly, output conduit 30 has only one part 38-1 of a two-part connector 38 connected thereto. The mating parts 38-2 for two-part connector 38 of input and output conduits 36, 30 are in liquid communication with processing line or vessel (A).

Figure 7:
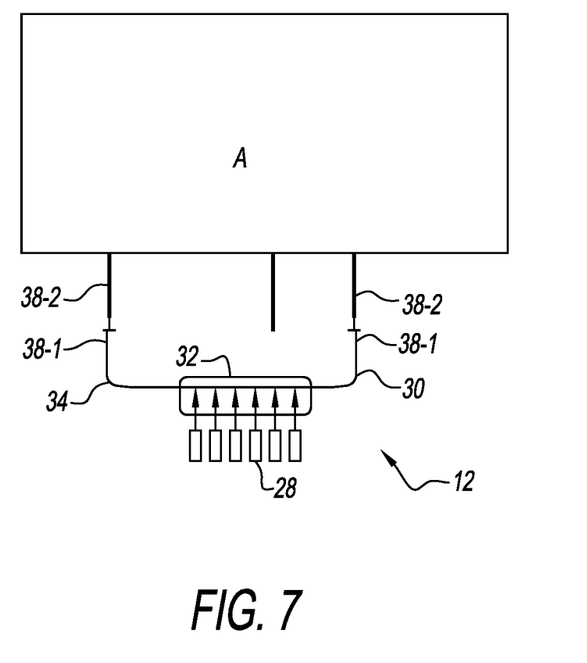
FIG. 7 is a schematic view of a liquid collection set in use with a vaccine production vessel.

Liquid collection device 12 can be liquidly connected to the processing line or vessel (A) by joining both halves 38-1, 38-2 of two part-connector 38 at input conduit 34 and the processing line or vessel A to one another and by joining both halves 38-1, 38-2 of two part-connector 38 at output conduit 30 and the processing line or vessel A to one another. In this manner, liquid collection device 12 forms a continuous closed loop with the processing vessel (A) as seen in FIG. 7.

It has been determined by the present disclosure that, during the manufacture of products that use live viruses, the inactivation of such viruses are often performed using a chemical disinfectant. When using chemical disinfectants, it is necessary for the liquid within the processing vessel (A) to be continuously mixed and recirculated such that dead legs or zones of reduced mixing and flow are eliminated or kept to a minimum. Further, during this chemical reduction of viruses, it is necessary to a number of different samples to see how much reduction of live virus has taken place.

Advantageously, the use of device 12, which forms a continuous loop with vessel (A) has been found to allow the necessary samples to be taken and to mitigate dead legs from the system. Moreover, the use of device 12 allows vessel (A) to be a closed vessel so that the risk of exposure to live virus is reduced and the risk of sterility failure is reduced.

In order to maintain sterility, the portion of the two-part connector 38-2 mated with the production line or vessel (A) can be sterilized or sanitized along with the production line or vessel before processing of the liquid.

Two-part connectors 38 can be any disposable, two-part aseptic connector such as, but not limited to the Kleenpak™ connector, which is commercially available from Pall Corporation, the Opta® SFT-I connector, which is commercially available from Sartorius Stedim Biotech, the Lynx® ST connector, which is commercially available from Millipore Corporation, and the AseptiQuik™ connector, which is commercially available from Colder Products Corporation.

In some embodiments of liquid collection device 12, product collection containers 28 and valve block 32 are removably connected to one another. For example, liquid collection device 12 can include a plurality of connectors 39 such as, but not limited to Luer lock connectors.

All product contact surfaces within collection device 12 are made of any material sufficient to hold or contact the liquid without interacting or contaminating the liquid. Moreover, collection device 12 can be packaged within one or more outer wrappings (not show) then can be sterilized using known sterilization methods such as, but not limited to, gamma irradiation. In this manner, collection device 12 can remain in a sterile condition until ready for use.

Figure 6:
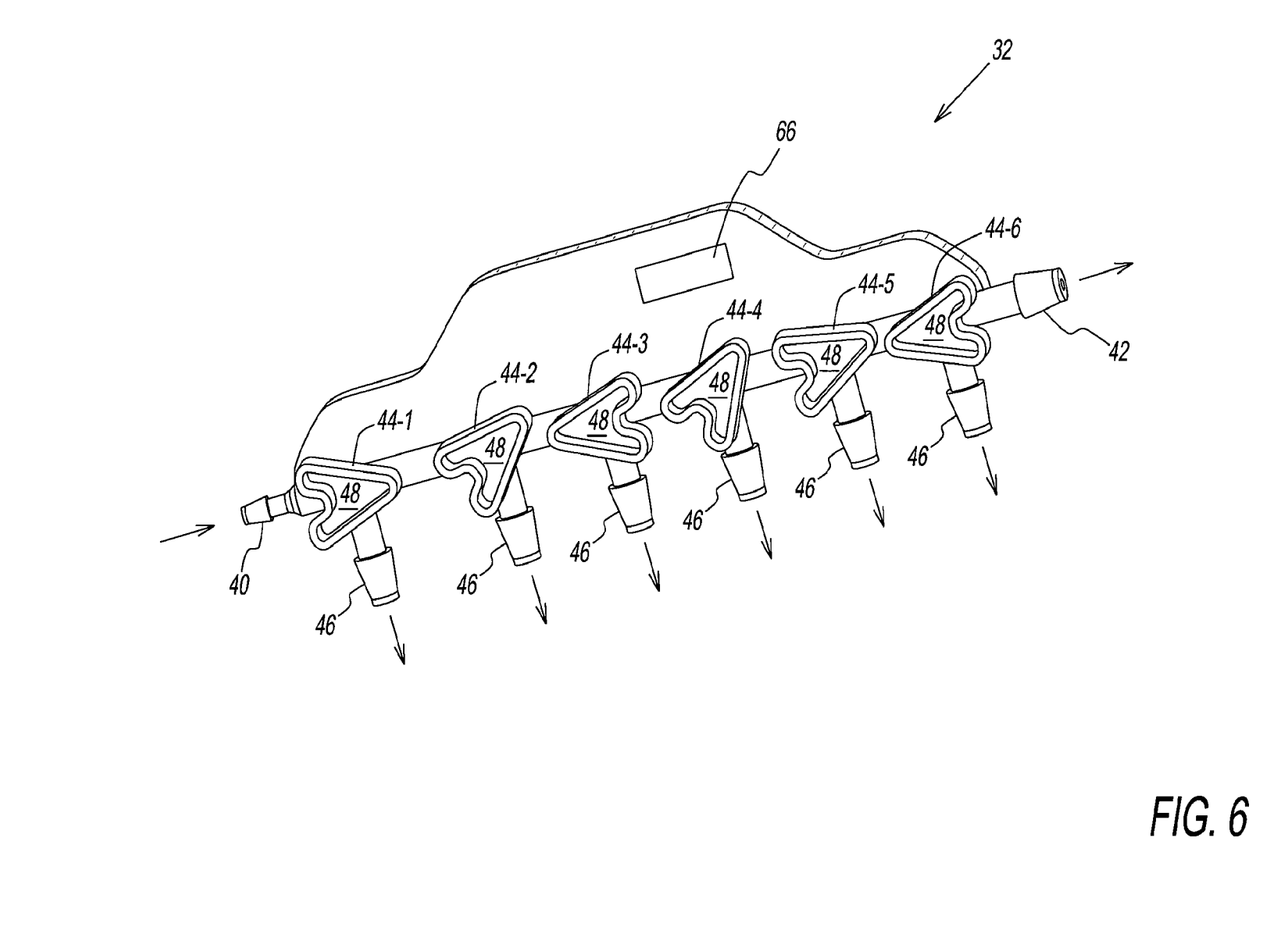
FIG. 6 is a perspective view of an exemplary embodiment of a valve block according to the present disclosure for use in the liquid collection set of FIG. 5.

Valve block 32, as shown in FIG. 6, includes an input 40, an output 44, and a plurality of valves 46 (six shown). The input 40 is in liquid communication with input conduit 34 and output 42 is in liquid communication with output conduit 30.

Valves 44 correspond in number to the plurality of collection containers 28, with an output 46 from each of the valves being in liquid communication with a different collection container 28.

Valves 44 are each movable by rotation of a valve handle 48 among at least two positions: a "recirculate" position and a "collection" position.

In the recirculate position, each valve 44 allows liquid from input 40 to flow through the valve towards waste output 42, but prevents flow toward its respective output 46. In the collection position, each valve 44 allows liquid from input 40 to flow through the valve towards the respective output 46, but prevents flow toward the waste output 42.

Handle 48 of each valve 44 operably mates with a different portion of valve actuator 22 so that the valve actuator can selectively rotate each handle independently of one another among the three positions. In this manner, workstation 10, via valve actuator 22, is configured to actuate valve block 32 to selectively divert liquid from the processing line or vessel (A) into any one of collection containers 28 or return the liquid back into the processing line or vessel.

Referring now to Table No. 1 below, the relative positions of valves 44 are provided during various sampling activities contemplated by the present disclosure.

Here, the plurality of valves 44 are sequentially numbered, in the direction of liquid flow, as valves 44-1 through 44-6 and the collection containers 28 are sequentially numbered, in the direction of liquid flow, as containers 28-1 through 28-6.

tained therein, at a desired temperature. In other examples, workstation 10 can include agitation and/or vibration devices sufficient to maintain the liquid within containers 28 in a mixed or agitated state.

Workstation 10 can include one or more sensors 52 to monitor and record the conditions (e.g., temperature, humidity) within base 14, the conditions within containers 28 (e.g., temperature, turbidity, volume, etc), and other conditions of the workstation. Additionally, workstation 10 can include sensors or can connect to sensors outside 54 the workstation to monitor and records the conditions outside the base 12 including but not limited to temperature, pressure, humidity, particulates, and detection, typing and monitoring of viral and/or microbial organisms.

It is contemplated by the present disclosure for workstation 10 to coordinate the control of pump 20, valve actuator 22, liquid edge detector 24, and sensors 50 within workstation 10 as well as collection of signals and data from any other (wireless or hardwire connected) human-machine

TABLE NO. 1

| | VALVE POSITION | | | | | |
|---|---|---|---|---|---|---|
| | Valve 44-1 | Valve 44-2 | Valve 44-3 | Valve 44-4 | Valve 44-5 | Valve 44-6 |
| Return liquid to line A | Recirculate | Recirculate | Recirculate | Recirculate | Recirculate | Recirculate |
| Collect in container 28-1 | Collection | Recirculate | Recirculate | Recirculate | Recirculate | Recirculate |
| Collect in container 28-2 | Recirculate | Collection | Recirculate | Recirculate | Recirculate | Recirculate |
| Collect in container 28-3 | Recirculate | Recirculate | Collection | Recirculate | Recirculate | Recirculate |
| Collect in container 28-4 | Recirculate | Recirculate | Recirculate | Collection | Recirculate | Recirculate |
| Collect in container 28-5 | Recirculate | Recirculate | Recirculate | Recirculate | Collection | Recirculate |
| Collect in container 28-6 | Recirculate | Recirculate | Recirculate | Recirculate | Recirculate | Collection |

As seen in Table No. 1 above, when liquid collection device 12 is not in use, all of the valves 44 are rotated to the "recirculate" position, allowing liquid communication from input conduit 34 through valve block 32 to output conduit 30.

When diversion of liquid to a particular collection container 28 is desired, the particular valve 44 associated with that particular container 28 is moved to the "collection" position, while all other valves are retained in the "recirculate" position.

In use, liquid collection device 12 is positioned in workstation 10 so that flexible portion 36 of input conduit 34 is operatively positioned in pump 20 and valve block 32 is operatively positioned in valve actuator 22. Here, the half of two-part connector 38 at input conduit 34 is operatively connected to its mating half arranged on the line or vessel (A) and the half of two-part connector 38 at output conduit 30 is operatively connected to its mating half arranged on the line or vessel (A).

In this manner, valve actuator 22 can be automatically controlled by workstation 10 as described in more detail herein below to collect samples according to a desired protocol. It should be recognized that workstation 10 is discussed above by way of example as including pump 20. However, it is contemplated by the present disclosure for processing line or vessel (A) to be pressurized or have its own liquid circulation device such that no additional pump is required.

Workstation 10 can, in some embodiments, include a sample container holding area 50, which can maintain containers 28 in a desired position and/or in a desired condition suitable for the liquid contained therein. For example, workstation 10 can include environmental controls sufficient to maintain containers 28, and thus, liquid coninput devices 56 such as, but not limited to, keyboards, and touch screens or any other data communication devices, USB or other data communication ports, CD or other data reading devices, computers, PLC's, analyzing equipments, testing devices and sensors outside the workstation.

In some embodiments, liquid collection device 12 can include a disposable flow meter 58 in electrical communication with workstation 10.

Thus, workstation 10 can include a processor 60 having human-machine-interface (HMI) 56 with one or more input devices 62 and one or more output devices 64. Processor 60 can include devices such as, but not limited to, a computer, a programmable logic controller (PLC), or any other processor suitable to control the various components of workstation 10.

HMI 56 can includes, for example, a keyboard, a mouse, a bar-code reader, a touch screen, a USB or other data communication port, CD or other data reading device, a remote control, or any other data communication device suitable for inputting commands to processor 60 in a wired and/or a wireless manner, and any combinations thereof.

Output device 64 can include a computer monitor, an audible alarm device, a visual alarm device, a printer, a USB or other data communication port, a CD or other data writing device, a (wireless or hard-wired) data communication device or any other device suitable for receipt of a wired and/or a wireless output from processor 60.

In a preferred embodiment, HMI 56 includes at least one bar code reader 62 and liquid collection device 12 can include at least one machine readable label 66, which includes details regarding the liquid collection device such as, but not limited to, the lot number, the expiration date, the number of product containers 28, the volume of product containers 28, the volume of conduits within the collection device, and other details. In use, the operator can scan machine readable label 66 of liquid collection device 12 using bar code reader 62 so that processor 60 can determine and record the various details regarding the liquid collection device 12.

Further, it is contemplated by the present disclosure for output devices 64 to include at least one printer. Processor 60 controls printer 64 to print labels, which can be applied by the operator directly on each container 28 and includes information that is relevant to the liquid contained within the container. For example, processor 60 can control printer 64 to print information such as, but not limited to, date of collection, time of collection, operator, batch ID, program sequence, room number, station number, collection location, and other process or environmental variables.

Preferably, printer 64 is configured to print information on the label in a machine readable language, such as a bar code, so that a laboratory technician can scan the machine readable code to input all relevant data related to the liquid within the container, which can mitigate instances of data entry errors.

Processor 60 is in electrical communication via any wireless or wired manner such as, but not limited to, electrical, optical, audible, infrared, radiofrequency, magnetic and other means of communication with any one or more of pump 20, valve actuator 22, level sensor 24, manual controls 48, sensors 52 and 54, HMI 56, flow meter 58, output devices 60, as well as bar code reader 62 and printer 64.

In this manner, processor 60 is configured to coordinate the control of workstation 10 and the collection of liquid in collection device 12, as well as to provide information on labels for placement onto containers 28.

In some examples, processor 60 can communicate in wired and/or wireless manner with one or more computers (not shown) external to workstation 10, where such external computers can include data collection, data archiving, data analysis and data management software.

The aseptic liquid collection ability of workstation 10 and collection device 12 mitigate or eliminate the risk of contaminating the collected liquid or the processing line.

Workstation 10, via processor 60, can be programmed to aseptically obtain one or a series of liquid collections taken randomly, at manual selected times or at pre-set times and with manually selected volumes or pre-set volumes.

Figure 8:
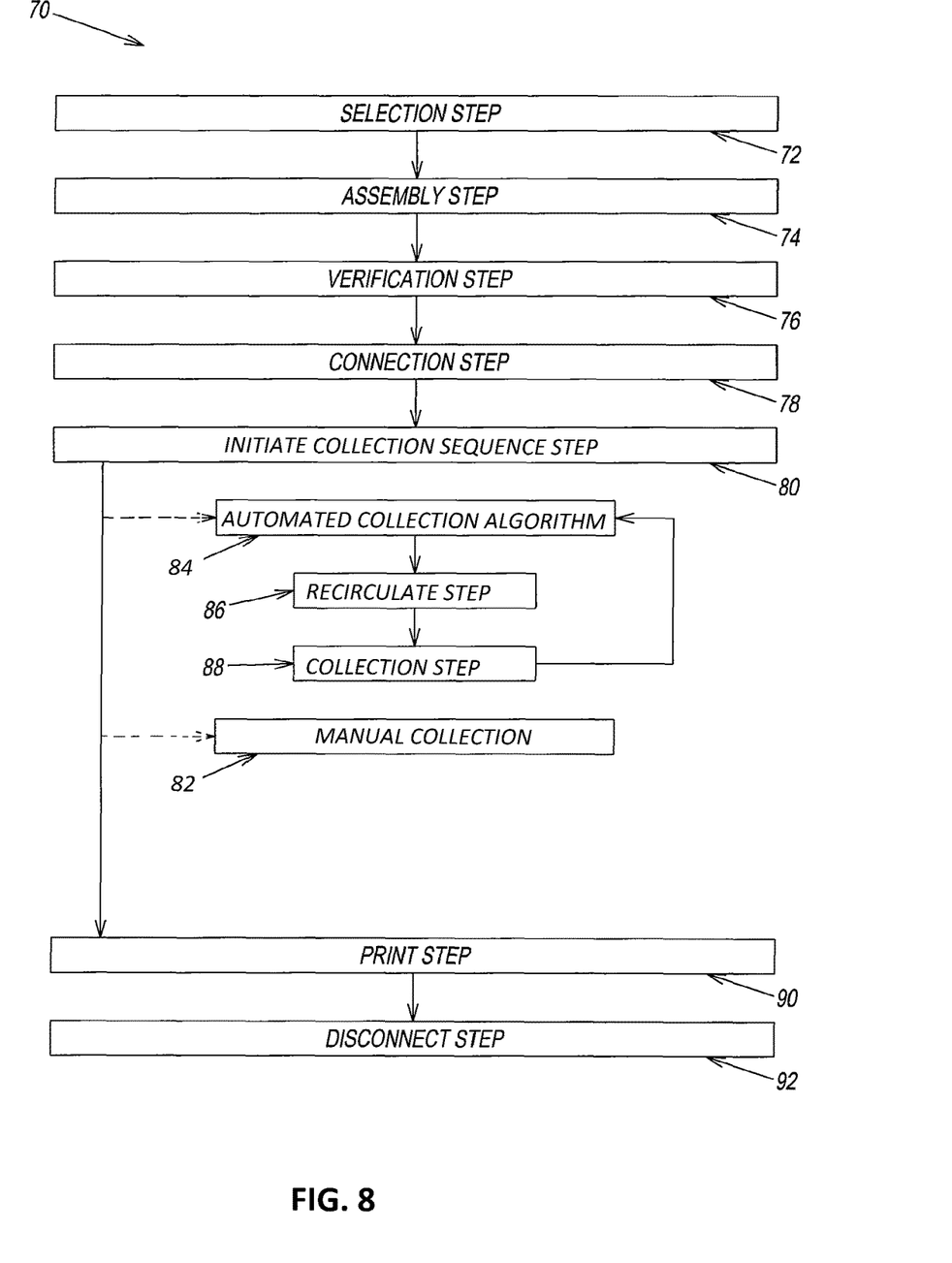
FIG. 8 is a flowchart illustrating an exemplary embodiment of a liquid collection method for detecting virus deactivation according to the present disclosure.

Referring now to FIG. 8, a method 70 of operating workstation 10 having liquid collection device 12 during virus deactivation is shown.

In a first or selection step 72, the appropriate liquid collection device 12 for desired collection is selected by the operator.

In a second or assembly step 74, the operator assembles the selected liquid collection device 12 in workstation 10. Specifically, containers 28 are placed in area 50 and valve block 32 is operatively positioned in valve actuator 22. When pump 20 is present, flexible portion 36 of input conduit 34 can be operatively positioned in the pump. Additionally, when level liquid edge detector 24 is present, a portion of input conduit 34 can be operatively positioned in the detector.

In a third or verification step 76, the operator inputs information related to the liquid collection device 12 into processor 60 and inputs information related to the desired processing line or vessel (A) from which workstation 10 will be collection the liquid. In some embodiments, the verification step 76 includes requiring the operator to use scanner 62 to scan bar code 66 on liquid collection device 12.

Once processor 60 verifies liquid collection device 12, the processor sends an output to the operator in a fourth or connection step 78 to instruct the operator to place the liquid collection device in liquid communication with the processing line or vessel (A) via HMI 56. As discussed in detail above, liquid collection device 12 is placed in liquid communication with the processing line or vessel (A) by interconnecting two-part connectors 38 of both input and output conduits 34, 30 to the vessel.

The operator initiates a desired collection sequence of workstation 10 during step 80. Step 80 may initiate a manual collection process 82 using manual controls 48. Alternately, step 80 may initiate an automated collection process using an algorithm 84 resident on processor 60.

During automated collection, algorithm 84 is configured to activate pump 20 to force liquid from the processing line or vessel (A) through input conduit 34, valve block 32, and through output conduit 30 back into the vessel. In this recirculation step 86, algorithm 84 controls valve actuator 22 to ensures that all valves 44 are in the recirculate position.

Then, when a sample is required, algorithm 84 controls, at a collection step 88, workstation 10 to activate valve actuator 22 to move the desired valve 44 to the collection position for a period of time sufficient, based on the flow rate of liquid through collection device 12, to collect a sample of desired volume in container 28. Once the sample is collected, algorithm 84 controls, at collection step 88, workstation 10 to activate valve actuator 22 to return valve 44 to the recirculation position in the manner discussed above with respect to Table No. 1.

Algorithm 84 repeats the recirculate and collection steps 86, 88 until all of the desired liquid collections have been obtained.

In embodiments where liquid collection device 12 includes flow meter 58, algorithm 84 can use inputs from the flow meter to ensure proper sample volumes. Similarly, in embodiments where workstation 10 includes liquid edge sensor 24, algorithm 84 can use inputs from the sensor to ensure proper sample volumes.

Preferably, algorithm 84 is further configured to activate printer 64 to print data onto a label when a respective collection of liquid is obtained during a print step 90. The operator can then apply the label on the appropriate container 28, respectively.

Once all of the collections of liquid have been obtained, the operator can, during a disconnection step 92, disconnect liquid collection device 12 from the processing line or vessel by separating two-part connectors 38 at both the input and output conduits 34, 30. Similarly, the operator can remove each product container 28 from liquid collection device 12 by separating two-part connectors 38.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the present disclosure.

What is claimed is:

1. An automated liquid collection workstation, comprising:
   A processor;
   A peristaltic pump in electrical communication with said processor;
   A valve actuator in electrical communication with said processor, said valve actuator configured to move a plurality of valves, when the plurality of valves are operatively associated with said valve actuator, between a recirculate position and a collection position; and
   An algorithm encoded on said processor, said algorithm configured to:
      Move all of said plurality of valves to the recirculate position and place said pump in a on state when recirculation is required; and
      Move a respective one of said plurality of valves to said collection position for a predetermined collection time period while leaving said pump in said on state when a collection is required.

2. The liquid collection workstation of claim 1, further comprising a bar code scanner in electrical communication with said processor so that machine readable code, when scanned by said bar code scanner, is input to said processor.

3. The liquid collection workstation of claim 1, further comprising a label printer in electrical communication with said processor so that the processor controls the label printer to print labels comprising information relevant to said collection.

4. The liquid collection workstation of claim 1, further comprising a liquid edge detector in electrical communication with said processor, said processor controlling said liquid edge detector to detect when liquid is present.

5. The liquid collection workstation of claim 1, further comprising a sensor in electrical communication with said processor, said sensor being configured to detect an environmental condition.

6. The liquid collection workstation of claim 1, further comprising a base in which said processor, peristaltic pump, and valve actuator are disposed.

7. The liquid collection workstation of claim 6, wherein said base further comprises a product container holding area, which can maintain a product container in a desired position and/or in desired conditions suitable for the liquid contained therein.

8. An automated liquid collection workstation, comprising:
   A valve actuator configured to operably and removably mate with a plurality of valves of a liquid collection device so as to selectively rotate each of the plurality of valves independently of one another between a recirculate position and a collection position;
   A pump configured to removably and operably receive a portion of the liquid collection device so that said pump pumps a fluid through the liquid collection device; and
   A processor programmed with an algorithm to move all of the plurality of valves to the recirculate position and place said pump in an on state when recirculation of the fluid through the liquid collection device is required and move a respective one of the plurality of valves to the collection position for a predetermined collection time period while leaving said pump in the on state when a collection of the fluid is required.

9. The liquid collection workstation of claim 8, further comprising a bar code scanner in communication with said processor so that machine readable code, when scanned by said bar code scanner, is input to said processor.

10. The liquid collection workstation of claim 8, further comprising a label printer in communication with said processor so that the processor controls the label printer to print labels comprising information relevant to said collection.

11. The liquid collection workstation of claim 8, further comprising a liquid edge detector in communication with said processor, said processor controlling said liquid edge detector to detect when liquid is present in a predetermined location in the liquid collection device.

12. The liquid collection workstation of claim 8, further comprising a sensor in communication with said processor, said sensor being configured to detect an environmental condition.

13. The liquid collection workstation of claim 8, further comprising a base in which said processor, pump, and valve actuator are disposed.

14. The liquid collection workstation of claim 13, wherein said base further comprises a product container holding area, which can maintain a product container in a desired position and/or in desired conditions suitable for the liquid contained therein.

* * * * *